United States Patent [19]

Haker

[11] 4,022,419

[45] May 10, 1977

[54] MOULD FOR MAKING AND HOLDING WORKING MODELS FOR THE MANUFACTURE OF DENTAL PROSTHESES

[76] Inventor: Gerd Haker, Holstenstrasse 73, 2000 Hamburg 50, Germany

[22] Filed: Aug. 21, 1975

[21] Appl. No.: 606,451

[30] Foreign Application Priority Data

Aug. 22, 1974 Germany .......................... 2440261

[52] U.S. Cl. .................................. 249/54; 32/71; 425/175
[51] Int. Cl.[2] ................... A61C 9/00; B29C 1/16
[58] Field of Search ....... 249/117, 118, 54, DIG. 1; 425/179, 180, 175; 32/2, 11, 32, 71

[56] References Cited

UNITED STATES PATENTS

| 85,605 | 1/1869 | Musgrove | 249/DIG. 1 |
| 105,992 | 8/1870 | Smith | 249/DIG. 1 |
| 2,700,219 | 1/1955 | Lindley | 32/32 |

Primary Examiner—Robert L. Spicer, Jr.
Assistant Examiner—John S. Brown
Attorney, Agent, or Firm—Stevens, Davis, Miller & Mosher

[57] ABSTRACT

A mould for making and holding a model used to make false teeth has a base part having internally ribbed outwardly inclined sidewalls and retaining means for holding a model in the base. The ribs enable the model to be repositioned exactly in the mould even if after manufacture the model has been sawn into several pieces.

5 Claims, 9 Drawing Figures

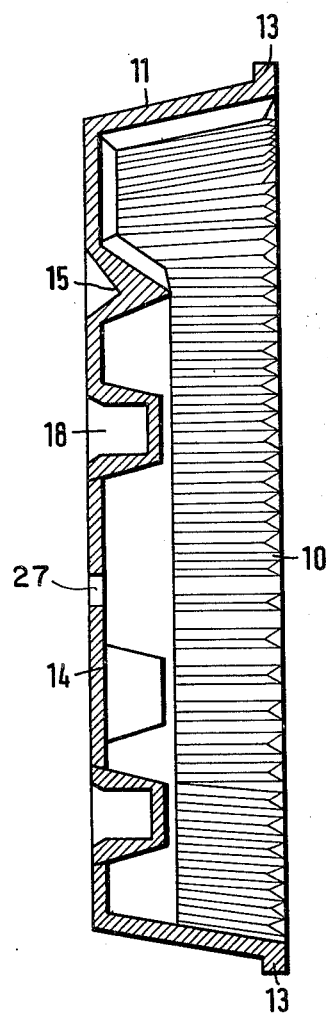
Fig.3 (A-B)
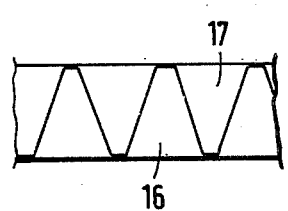
Fig.9

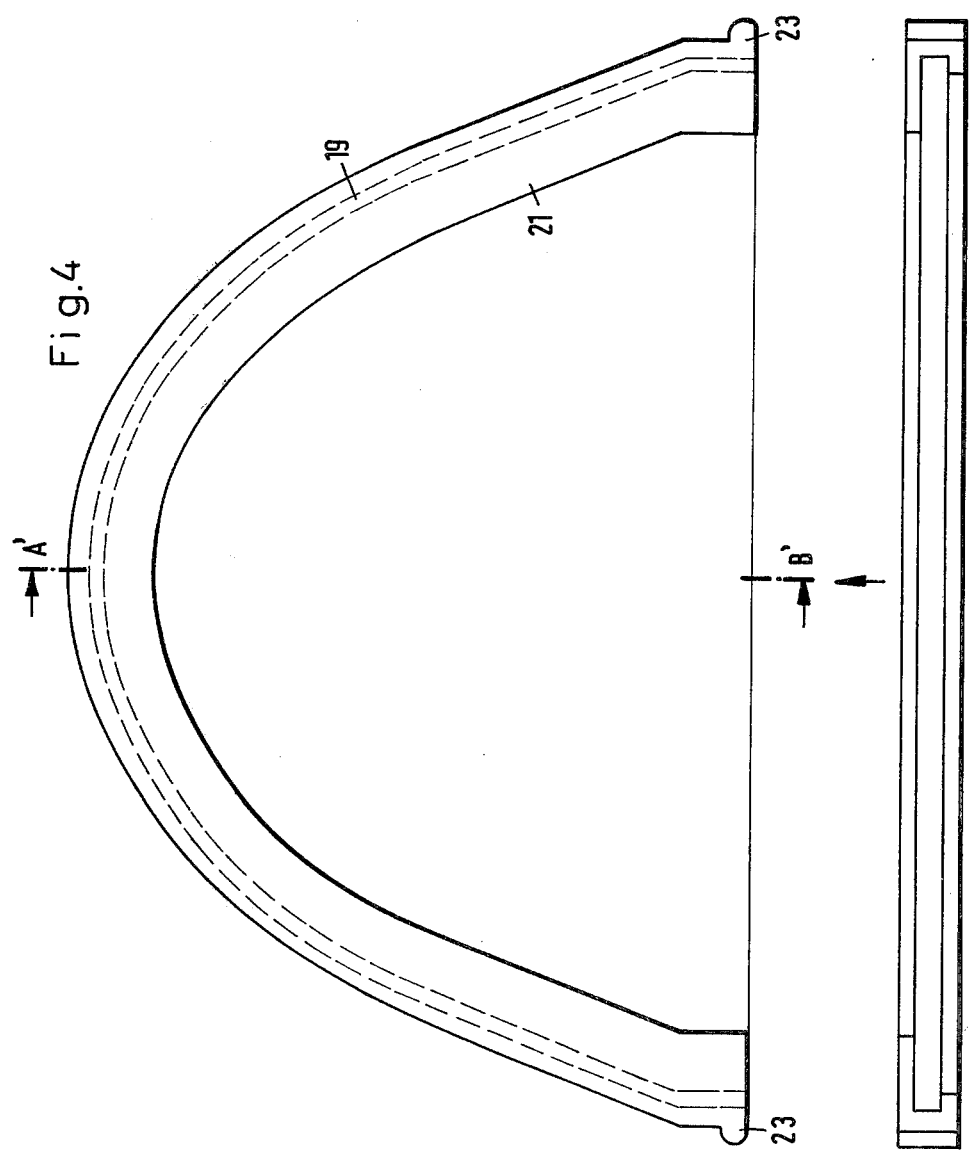

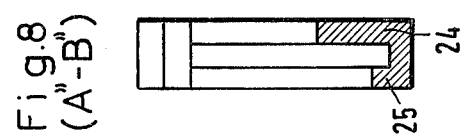
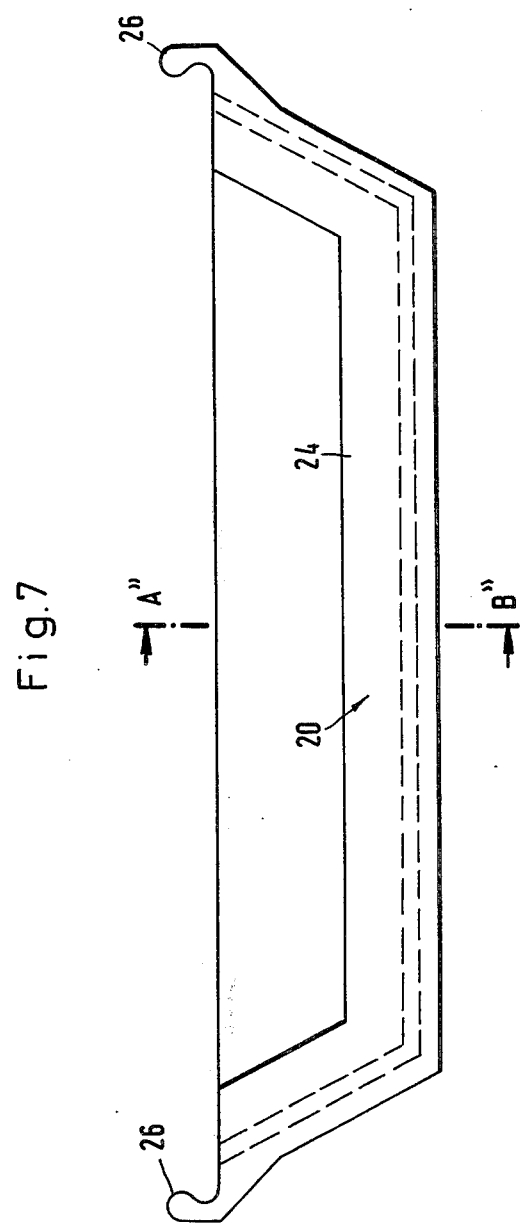

MOULD FOR MAKING AND HOLDING WORKING MODELS FOR THE MANUFACTURE OF DENTAL PROSTHESES

The invention relates to a mould for making and holding working models for the manufacture of dental prostheses.

In the current state of the art, numerous types of various construction and composition are known for receiving working models for making dental prostheses. In order to make replacement teeth, a print or moulding of the upper or lower jaw or both is made by the dentist and this impression is then sent to the dental technician to prepare false teeth. The dental technician provides himself with a working model from the print made by the dentist, for example proceeding as follows: the impression is filled with plaster and further a plaster composition is introduced into a mould roughly of the shape to be manufactured and before the plaster is hardened, the plaster of the working model and the plaster base are pressed together in the mould, the excess plaster is removed and after hardening of the plaster the working model and the base firmly connected therewith are removed from the mould and further worked on.

For the manufacture of false teeth it is necessary to saw the working model and the base firmly bonded thereto into pieces in order to be able to carry out on the parts of the working model precise work for the manufacture of the false teeth. It is however necessary (particularly in the case of work for an upper jaw) to be able to reassemble the sawn apart parts of the working model exactly together and keep them in the shape.

In known moulds the separation and reassembly of the mould parts is comparatively difficult since the working model consists of a plurality of sawn up parts which must be installed in reassembled form exactly into their earlier position. The danger exists in this that if assembly is not carried out very carefully, parts of the plaster base and of the working model are damaged. Additionally the manufacture of such permanent moulds is comparatively very expensive since for the manufacture of such a model several part moulds with undercut portions have to be used.

A mould is known consisting of a base part and intermediate body into which the working model is introduced and in which between the base part and the intermediate body removable retention parts are provided near the floor of the mould.

According to the present invention there is provided a mould for the manufacture and receipt of a jaw impression working model for manufacturing false teeth and comprising retaining elements to hold the working model wherein the contours of the mould are approximately those of a working model and wherein the mould is constructed with side walls broadening outwardly somewhat from below to above and provided inwardly with ribs, the upper edges of the side walls being provided with guides to which the retaining elements directly engaging with one another can be releasably fixed, the retaining elements being provided with projections or hooks for holding the working model.

Such a mould for the receipt of working models for making false teeth enables the working models to be made, removed, sawn up and then in simple fashion reassembled into the mould in exactly their previous position. The mould of the invention is simple and inexpensive to manufacture and can if desired be used as a disposable mould.

According to a practical embodiment of the invention the retaining elements matching the shape of the mould are each provided with a flange engaging under a guide flange on the mould.

According to a further embodiment of the invention claws are provided on one retention element for engaging behind projections on the other retention element.

According to a further embodiment of the invention the mould is provided on its interior floor with a rib standing at a distance from the side walls and directed upwardly for additional holding of the working model.

The construction of the mould can be such that the mould which has in cross-section a somewhat U-shape widens somewhat with its side walls or U-shoulders along the greater part of the mould, which then tapers somewhat again. In this the one retaining element can extend over the whole of the broadening part of the mould while the second retention part extends over the rear wall and the part of the mould extending somewhat from the rear wall in such a shape that the retention parts can be latched to one another at the position of the greatest cross-section of the mould.

Because a plurality of grooves are constructed between the interior wall of the mould and the ribs, an exceptionally good holding of the individually sawn up parts of the combination consisting of working model and base is achieved, so that it is ensured that each sawn up part of the previously noted combination is again held in the mould in its exact position.

In one form of the invention in the floor of the mould there can be provided in the part of the mould limited by the inner rib means for facilitating the removal of the combination consisting of working model and base and this means can be constituted by an area of reduced thickness built into the base of the mould, which when the hardened combination is to be separated from the mould after the removal of the retaining elements, can be pressed through and thus guarantee a saitsfactory removal of the above noted combination from the mould.

In the mould according to the invention in the base of the floor of the mould in the part limited by the interior rib apertures can be formed. These apertures serve a purpose of receiving or forming a joint with retaining plugs which enter into the apertures on the base of the mould which can be fixed by plaster on setting into the device provided for this. After incorporation or jointing in with plaster into the known apparatus therefor in dental technology, the plug and plug devices serve for removal or repositioning of the model with the mould as guiding and holding elements.

According to one embodiment of the invention the space between the interior ribs is constructed open. This gives the possibility that this part can be used to receive the palate portion of a tooth replacement part.

In order to realize the invention it is not necessary that it has a substantially U-shaped form in cross-section. According to the impression made by the dentist, a half mould can also be formed which is substantially matched to the shape of one half of the upper or lower jaw.

By way of example the invention is illustrated with reference to the accompanying drawings, in which:

FIG. 3 shows a longitudinal section along the lines A − B of FIG. 1;

FIG. 4 shows on an enlarged scale a plan view of a retaining element or a retaining clasp;

FIG. 5 shows a cross-section according to lines A' − B' of FIG. 4;

FIG. 6 shows an end face view of the retaining element of FIG. 4;

FIG. 7 shows on an enlarged scale a plan view of a second retaining element;

FIG. 8 shows a cross-section through the second retaining element according to lines A" − B" of FIG. 7, and FIG. 9 shows on an enlarged scale a detail of the construction of the ribs.

Figure 1:
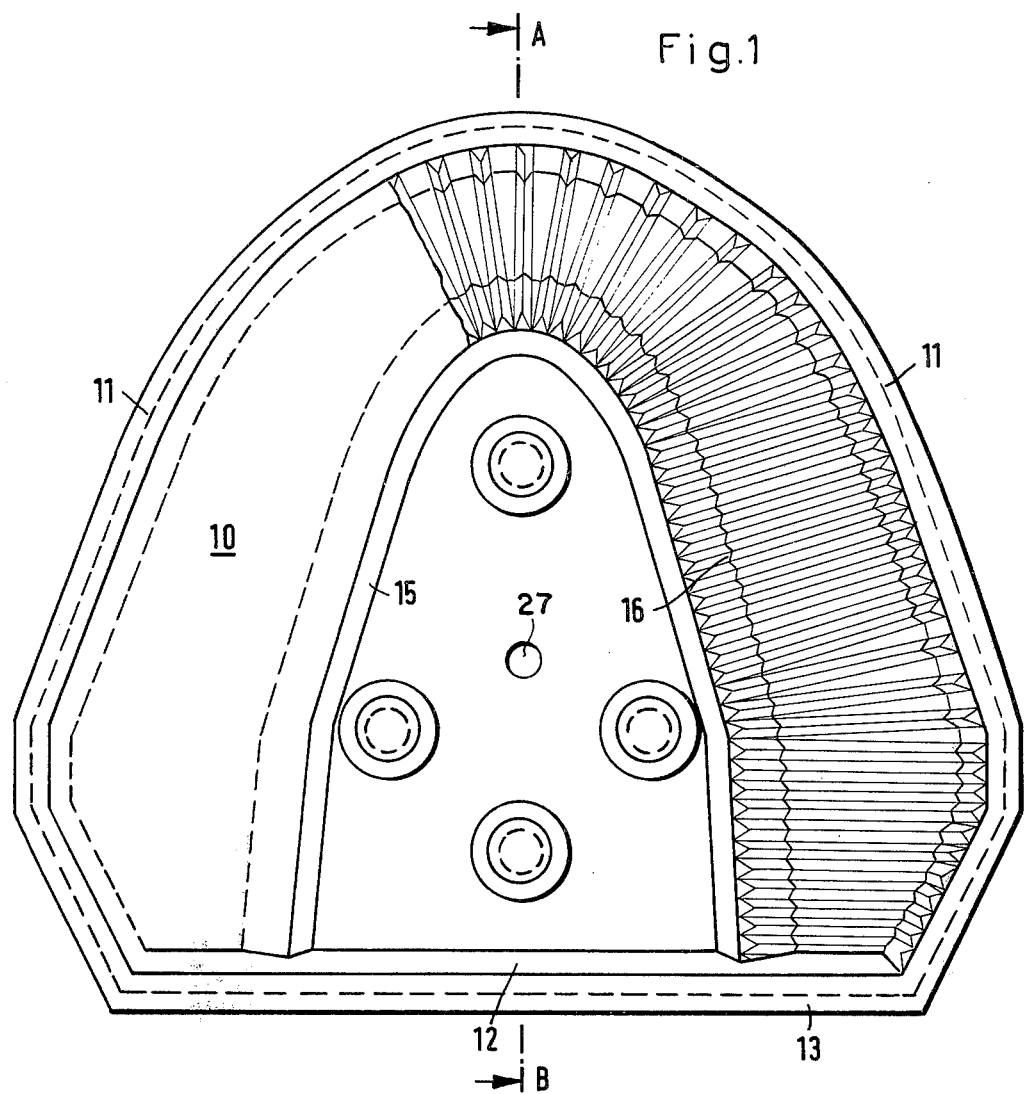
FIG. 1 shows a plan view of the mould according to the present invention.
Figure 2:
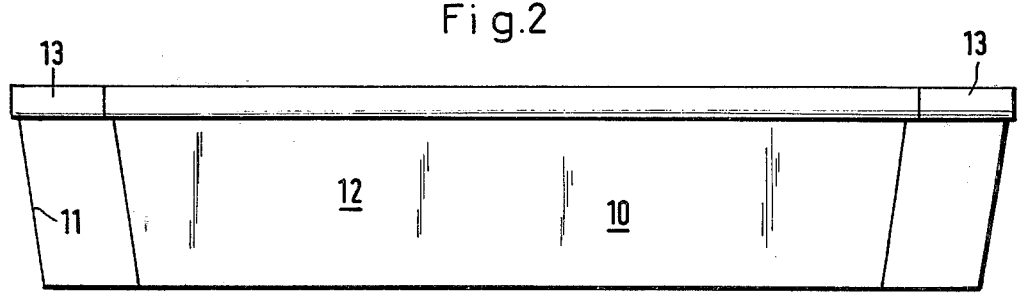
FIG. 2 shows an end view of the mould seen from the flat rear wall.

A mould is generally denoted at 10 which has in plan and section substantially a U-shape the shoulders of which broaden somewhat outwardly and then come together again. The mould 10 has a side wall denoted 11 and a rear wall denoted 12. The side wall 11 runs, as is evident from FIG. 3, from the base 14 of the mould 10 upwardly and outwardly. The side wall 11 and the rear wall 12 are provided at their upper end with circumferential outwardly directed guide flanges 13. Extending from the floor 14 of the mould 10 and at a distance from the side wall 11 there is a peripheral rib 15 which extends only over part of the height of the mould as is evident from FIG. 3. The wall portion 11, part of the floor 14 and one face of rib 15 are provided on their surfaces with a plurality of small ribs denoted 16, the cross-section of which diminishes from the base or from the walls as is evident from FIG. 9. By means of this a plurality of grooves denoted 17 are formed into which plaster can enter. In the underside of the floor 14 of mould 10 within the rib 15 there are provided several apertures 18. In the embodiment illustrated four such apertures 18 are provided the walls of which are constructed integrally with the floor 14 of mould 10. The walls of these apertures 18 extend substantially vertically from the floor 14.

For holding sawn parts of the combination of working model and base in the mould 10, two retention elements are provided in the form of a clasp 19 and a latch part 20. (compare FIGS. 4 to 8). The clasp 19, the shaping of which is matched to the broadening contour part of the mould 10 is provided with a flange 21 extending inwardly (compare FIGS. 4 and 5). Further it is provided at a distance from flange 21 with a further flange 22 so that the flange parts 21 and 22 in the working position engage over and below the guide flange 13 constructed on mould 10. The clasp 19 is provided on each of its ends with an outwardly extending projection 23 in the form of an engaging part.

The second retaining element 20 likewise has an inwardly directed flange 24 and on the underside a flange 25 at a distance from flange 24. On the ends of the second retaining element 20 in each case there is provided a claw portion denoted 26 which in the working position of the second retaining element 20 elastically engages the projections or claws 23 of the first retaining part 19 and thus latches the retaining parts 19 and 20 releaseably together in the working position.

Before carrying out work the retention elements 19 and 20 are so applied to the mould 10 that the retention elements are located in the latched condition. Then in known fashion the impression provided by the dentist an the mould 10 are cast with plaster and, before the plaster is bonded, the plaster model is set on the plaster in the mould 10 and the excess removed. After binding and hardening of the plaster and after unlatching and removing retaining parts 19 and 20 the combination of working model an base can be removed by pushing through the base 14 of the mould 10 (at 27) to release it from the mould 10. The working model with the base can now be sawn into however many parts are desired and the small model elements so arising can again be put back into the mould 10. The precise guidance of the individual mould parts is thereby guaranteed by means of the grooves 17 in the trough of mould 10 and by repositioning retention parts 19 and 20 again, the whole is set immovably, with parts of the working model engaged under flange 21 of the retention part 19 and parts engaged under the flange 24 of the second retention element 20.

The firmly and immovably held working model with the base can then be set using the mould itself into an occludator or articulator, this particularly when it is a case of manufacturing upper jaw dental prostheses. For this purpose retaining plugs are led into the apertures 18 in floor 14 of mould 10 and the plaster fixed on setting into the device provided therefor.

The mould or half mould of the invention can be made from a suitable material; preferably it is made by injection moulding from polystyrene which is comparatively inexpensive. By means of the invention a mould is manufactured by means of which in simple fashion a combination of base and working model can be made in the mould wherein further as a result of the plurality of grooves provided in the mould the sawn up working model pieces on being introduced into the mould automatically take up their correct position; as a result of the one piece construction of the mould can be securely held therein with the aid of the retention parts. As a result of its one piece construction the mould can be made with the aid of a single divided tool. The retention elements are suitably likewise made of the same plastics in simple fashion.

I claim:

1. A holder for the manufacture and receipt of a jaw impression working model for manufacturing false teeth, comprising a mould having a base, internally ribbed side walls extending from said base in a broadening manner, and a flange extending outwardly from said broadened walls at the top thereof and retaining elements contoured to the walls of the mould and removably attached to said flange, said retaining elements being provided with complementary projections at their ends to releasably hook said retaining elements together and hold the working model in position in the mould.

2. The mould according to claim 1, wherein said retaining elements which correspond to the contours of the mould are each provided with a flange engaging under the flange on said mould.

3. The mould according to claim 2, wherein the projections of one of said retaining elements are claws for engaging said projections on the other retaining element.

4. The mould according to claim 1, including an upwardly extending rib provided on the inner floor of the mould at a distance from the side walls to additionally hold the working model.

5. The mould according to claim 4, wherein with the exception of the floor of the mould the space within the inner rib is constructed open.

* * * * *